US011021839B2

(12) United States Patent
Konishi et al.

(10) Patent No.: US 11,021,839 B2
(45) Date of Patent: Jun. 1, 2021

(54) RECOVERY METHOD FOR ORGANIC ACID, AND PRODUCTION METHOD FOR RECYCLED PULP

(71) Applicant: Unicharm Corporation, Ehime (JP)

(72) Inventors: Takayoshi Konishi, Kanonji (JP); Toshio Hiraoka, Kanonji (JP); Takashi Kato, Kanonji (JP); Yoshihide Ishikawa, Kanonji (JP); Noritomo Kurita, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 16/759,482

(22) PCT Filed: Jul. 26, 2018

(86) PCT No.: PCT/JP2018/028154
§ 371 (c)(1),
(2) Date: Apr. 27, 2020

(87) PCT Pub. No.: WO2019/087488
PCT Pub. Date: May 9, 2019

(65) Prior Publication Data
US 2020/0332467 A1 Oct. 22, 2020

(30) Foreign Application Priority Data

Nov. 1, 2017 (JP) .............................. JP2017-212275
Jun. 1, 2018 (JP) .............................. JP2018-106352

(51) Int. Cl.
*D21C 5/02* (2006.01)
*D21C 9/00* (2006.01)
*D21C 11/00* (2006.01)

(52) U.S. Cl.
CPC ............... *D21C 5/022* (2013.01); *D21C 5/02* (2013.01); *D21C 9/005* (2013.01); *D21C 11/0007* (2013.01)

(58) Field of Classification Search
CPC ..................................................... D21C 5/022
See application file for complete search history.

(56) References Cited

U.S. PATENT DOCUMENTS 5,558,745 A * 9/1996 Conway ................. D21B 1/026
162/60
2010/0175691 A1 * 7/2010 Combs ..................... C08B 3/24
127/37
(Continued)

FOREIGN PATENT DOCUMENTS

EP       3064644 A1     9/2016
JP    2015182246 A     10/2015
(Continued)

OTHER PUBLICATIONS

PCT International Search Report dated Oct. 16, 2018 for Intl. App. No. PCT/JP2018/028154, from which the instant application is based, 2 pgs.
(Continued)

*Primary Examiner* — Anthony Calandra
(74) *Attorney, Agent, or Firm* — Fredrikson & Byron, P.A.

(57) ABSTRACT

The purpose of the present disclosure is to provide a recovery method for an organic acid. The recovery method makes it possible to efficiently recover an organic acid that is included in a deactivating aqueous solution that includes excrement. This recovery method has the following features. A method for recovering an organic acid that deactivates a highly water-absorbent polymer that is included in used absorbent articles, the method being characterized by including: a deactivation step (S1) in which the highly water-absorbent polymer is immersed in a deactivating aqueous solution that includes an organic acid and has a prescribed pH and the highly water-absorbent polymer is deactivated; a highly water-absorbent polymer removal step
(Continued)

(S2) in which the deactivated highly water-absorbent polymer is removed from the deactivating aqueous solution; a pH adjustment step (S3) in which the deactivating aqueous solution is adjusted to a prescribed pH; a concentration step (S4) in which the deactivation step (S1), the highly water-absorbent polymer removal step (S2), and the pH adjustment step (S3) are repeated using deactivating aqueous solution that has gone through the pH adjustment step (S3) and the organic acid in the deactivating aqueous solution is concentrated; and an organic acid recovery step (S6) in which the organic acid is recovered from the deactivating aqueous solution.

12 Claims, 6 Drawing Sheets

(56) References Cited

U.S. PATENT DOCUMENTS

2015/0045461 A1* 2/2015 Funamizu ............ B01J 20/3475
521/40

2017/0107667 A1 4/2017 Konishi et al.
2017/0305037 A1 10/2017 Konishi et al.

FOREIGN PATENT DOCUMENTS

| JP | 2016881 A | 1/2016 |
| WO | 2014203922 A1 | 12/2014 |
| WO | 2016059964 A1 | 4/2016 |
| WO | 2019087487 A1 | 5/2019 |

OTHER PUBLICATIONS

English Abstract for Japanese Publication No. 2016-000881 A, published Jan. 7, 2016, 1 pg.
English Abstract and Machine Translation for Japanese Publication No. 2015-182246 A, published Oct. 22, 2015, 38 pgs.
English Machine Translation for International Publication No. WO 2014/203922 A1, published Dec. 24, 2014, 17 pgs.
English Machine Translation for International Publication No. WO 2019/087487 A1, published May 9, 2019, 26 pgs.
Extended European Search Report for European Patent Application No. 18873055.0, dated Oct. 23, 2020, 7 pgs.

* cited by examiner

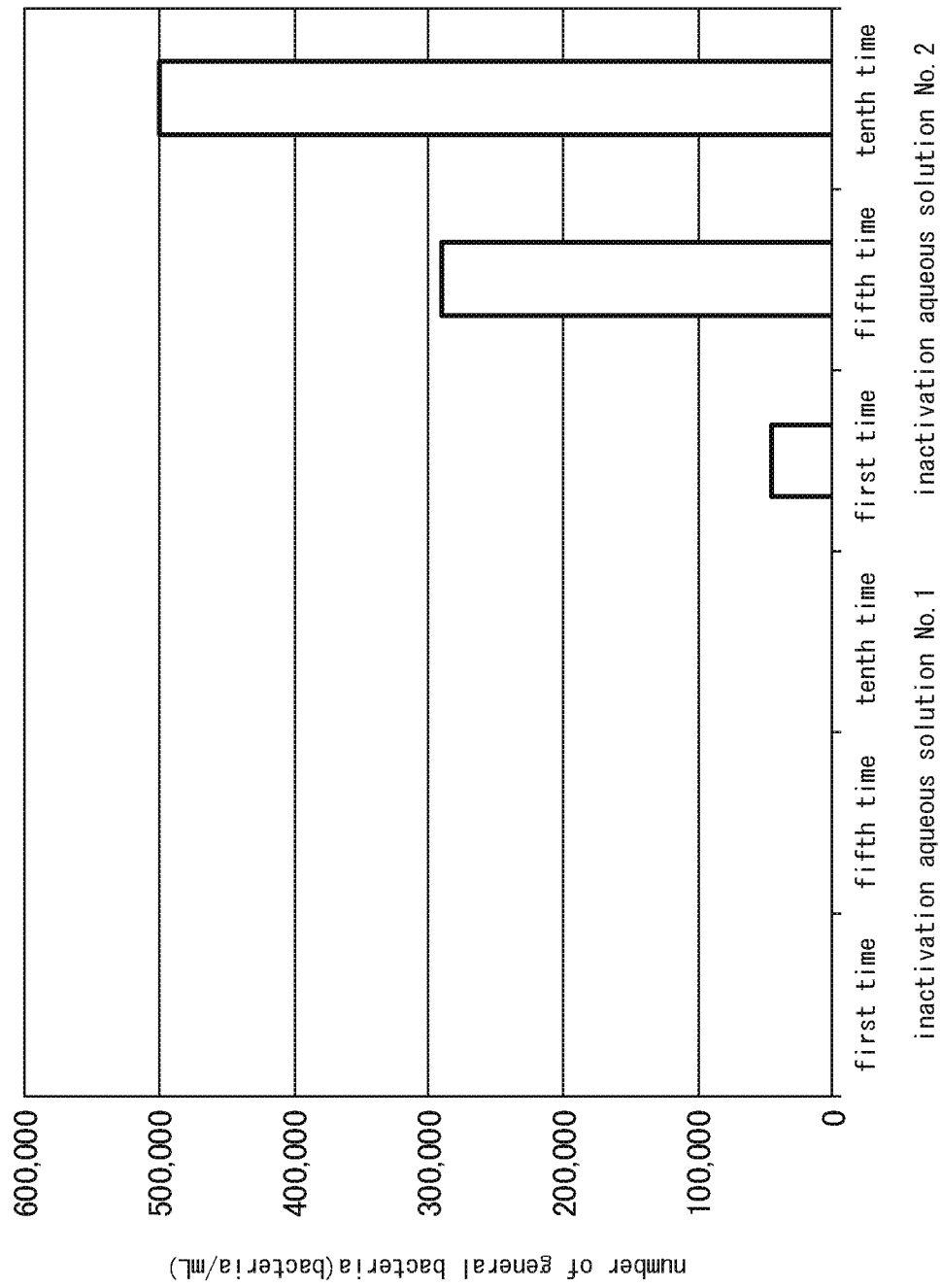

RECOVERY METHOD FOR ORGANIC ACID, AND PRODUCTION METHOD FOR RECYCLED PULP

RELATED APPLICATIONS

This application is a 35 U.S.C. 371 national phase filing from International Application No. PCT/JP2018/028154, filed Jul. 26, 2018, which claims priority to Japanese Application No. 2018-106352, filed Jun. 1, 2018 and Japanese Application No. 2017-212275, filed Nov. 1, 2017, the contents of which are incorporated herein by reference.

FIELD

The present disclosure relates to a method of recovering an organic acid which inactivates superabsorbent polymers included in a used absorbent article, and to a method of producing recycled pulp fibers from a used absorbent article while elevating a concentration of and recovering an organic acid which inactivates superabsorbent polymers,

BACKGROUND

Methods of recovering recycled pulp fibers from used absorbent articles are known.

For example, Patent Literature 1 discloses a method of recovering pulp fibers from used sanitary goods which include pulp fibers and superabsorbent polymers and producing recycled pulp which can be reused as sanitary goods, the method comprising: a decomposing step of decomposing the used sanitary goods into pulp fibers and other materials by applying a physical force to the used sanitary goods in an aqueous solution which includes polyvalent metal ions or an acidic aqueous solution which has a pH of 2.5 or less; a separating step of separating the pulp fibers from a mixture of the pulp fibers and the other materials which are generated in the decomposing step; and a treating step of treating the separated pulp fibers with an ozone which includes aqueous solution which has a pH of 2.5 or less.

Further, Patent Literature 1 discloses that an acidic aqueous solution which has a pH of 2.5 or less includes an organic acid, and that the organic acid is at least one type selected from the group consisting of tartaric acid, glycolic acid, malic acid, citric acid, succinic acid, and acetic acid.

CITATION LIST

Patent Literature

[PTL 1] Japanese Unexamined Patent Publication No. 2016-881

SUMMARY

Technical Problem

It is preferable to inactivate superabsorbent polymers by using an organic acid because many organic acids function as weak acids and have a small environmental load. On the other hand, when the superabsorbent polymers which include excrement of a wearer are inactivated, the excrement retained by the superabsorbent polymers is discharged into the inactivation aqueous solution, and therefore, in order to dispose of the inactivation aqueous solution which includes the excrement, treatment such as sterilization is necessary. In consideration of the environment, it is preferable to recover and reuse the organic acid which is included in the inactivation aqueous solution that includes the excrement.

Accordingly, it is an object of the present disclosure to provide a method of recovering an organic acid which can efficiently recover the organic acid which is included in an inactivation aqueous solution that includes excrement.

It is another object of the present disclosure to provide a method of producing recycled pulp which can produce recycled pulp fibers while efficiently recovering an organic acid which is included in an inactivation aqueous solution that includes excrement.

Solution to Problem

The present inventors have found a method of recovering an organic acid which inactivates superabsorbent polymers included in a used absorbent article, the method comprising: an inactivation step of inactivating the superabsorbent polymers by immersing the superabsorbent polymers in an inactivation aqueous solution which has a predetermined pH and includes an organic acid; a superabsorbent polymer removal step of removing the inactivated superabsorbent polymers from the inactivation aqueous solution which has been subjected to the inactivation step; a pH adjustment step of adjusting the inactivation aqueous solution which has been subjected to the superabsorbent polymer removal step to have a predetermined pH; a concentration elevation step of elevating a concentration of the organic acid included in the inactivation aqueous solution by repeating the inactivation step which uses the inactivation aqueous solution that has been subjected to the pH adjustment step, the superabsorbent polymer removal step, and the pH adjustment step; and an organic acid recovery step of recovering the organic acid from the inactivation aqueous solution which has been subjected to the concentration elevation step.

Advantageous Effects of Invention

The method of recovering an organic acid of the present disclosure can efficiently recover the organic acid which is included in an inactivation aqueous solution that includes excrement.

Further, the method of producing recycled pulp of the present disclosure can produce recycled pulp fibers while efficiently recovering an organic acid which is included in an inactivation aqueous solution that includes excrement.

BRIEF DESCRIPTION OF DRAWINGS

FIG. 6 shows the results of Examples 1 and 2.

DESCRIPTION OF EMBODIMENTS

Definition

"A Water-Insoluble Salt"

Figure 1:
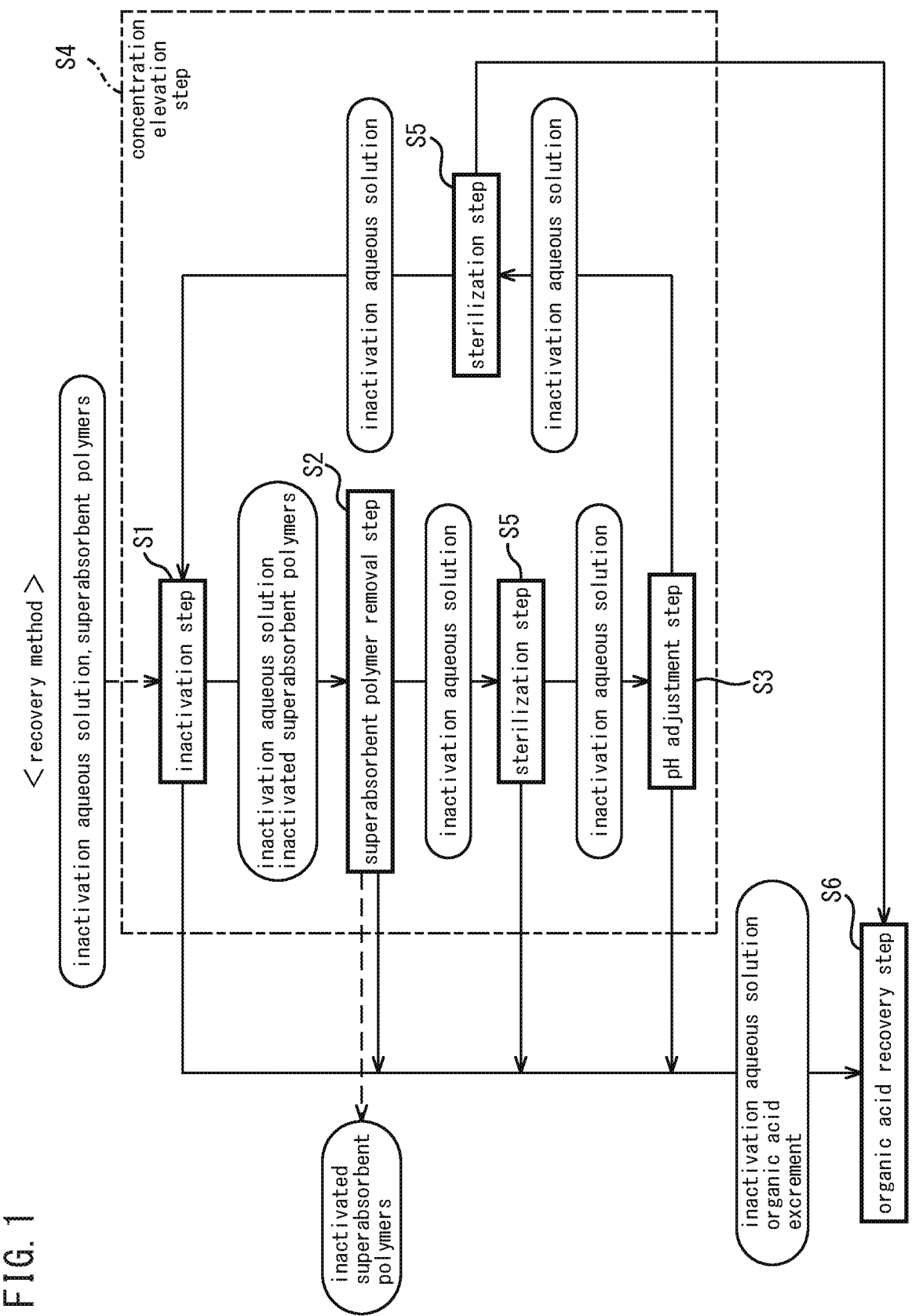
FIG. 1 is a flow chart for explaining the method of recovering an organic acid of the present disclosure.

In the present description, "water insoluble" with respect to "a water-insoluble salt" is preferably classified as "being difficult to dissolve," "being extremely difficult to dissolve," or "hardly soluble" in "General Rule 29" of the "Japanese Pharmacopoeia, 15th revision," more preferably classified as "being extremely difficult to dissolve" or "hardly soluble," and more preferably classified as "hardly soluble".

Specifically, "a water-insoluble salt" means that the amount of water in which 1 g of salt is dissolved within 30 minutes when 1 g of salt as a solute is put into water as a solvent and shaken strongly every 5 minutes for 30 seconds at 20±5° C., is as follows.
Being difficult to dissolve: 100 mL or more and less than 1,000 mL
Being extremely difficult to dissolve: 1,000 mL or more and less than 10,000 mL
Hardly soluble: 10,000 mL or more "A Water-Soluble Salt"

In the present description, "water-soluble" with respect to "a water-soluble salt" is preferably classified as "being relatively easy to dissolve," "being easy to dissolve," or "being extremely easy to dissolve," in "General Rule 29" of the "Japanese Pharmacopoeia, 15th revision", more preferably classified as "being easy to dissolve" or "being extremely easy to dissolve," and more preferably classified as "being extremely easy to dissolve".

Specifically, "a water-soluble salt" means that the amount of water in which 1 g of salt is dissolved within 30 minutes when 1 g of salt as a solute is put into water as a solvent and shaken strongly every 5 minutes for 30 seconds at 20±5° C., is as follows.
Being extremely easy to dissolve: less than 1 mL
Being easy to dissolve: 1 mL or more and less than 10 mL
Being relatively easy to dissolve: 10 mL or more and less than 30 mL The following categories are further present in the "General Rules 29" of the "Japanese Pharmacopoeia., 15th revision".
Being relatively difficult to dissolve:: 30 mL or more and less than 100 mL "Inactivation" With Respect to Superabsorbent Polymers In the present description, "inactivation" with respect to superabsorbent polymers (SAPs) means adjusting the superabsorbent polymers which retain excrement so as to have an absorption magnification of preferably 50 times or less, more preferably 30 times or less, and even more preferably 25 times or less, for example, letting the superabsorbent polymers release the retained excrement, suppressing absorption of the inactivation aqueous solution, etc.

The above-mentioned absorption magnification is measured as follows.
(1) The inactivated superabsorbent polymers are placed in a mesh and are suspended for 5 minutes, whereby moisture which is attached to the surface thereof is removed, and the mass thereof before drying (g) is measured.
(2) The inactivated superabsorbent polymers are dried at 120° C. for 10 minutes, and the mass thereof after drying: $m_2$ (g) is measured.
(3) The absorption magnification (g/g) is calculated by the following formula:

Absorption magnification $(g/g) = 100 \times m_1/m_2$

Incidentally, the inactivation aqueous solution means an aqueous solution for inactivating the superabsorbent polymers.

More specifically, the present disclosure relates to the following aspects.

Aspect 1

A method of recovering an organic acid which inactivates superabsorbent polymers included in a used absorbent article, the method comprising:
an inactivation step of inactivating the superabsorbent polymers by immersing the superabsorbent polymers in an inactivation aqueous solution which has a predetermined pH and includes an organic acid;
a superabsorbent polymer removal step of removing the inactivated superabsorbent polymers from the inactivation aqueous solution which has been subjected to the inactivation step;
a pH adjustment step of adjusting the inactivation aqueous solution which has been subjected to the superabsorbent polymer removal step to have a predetermined pit
a concentration elevation step of elevating a concentration of the organic acid included in the inactivation aqueous solution by repeating the inactivation step which uses the inactivation aqueous solution that has been subjected to the pH adjustment step, the superabsorbent polymer removal step, and the pH adjustment step; and
an organic acid recovery step of recovering the organic acid from the inactivation aqueous solution which has been subjected to the concentration elevation step.

In the above-mentioned method, the pH of the inactivation aqueous solution which inactivates the superabsorbent polymers is increased by the excrement which is retained by the superabsorbent polymers and is discharged as the superabsorbent polymers are inactivated, and the pH of the inactivation aqueous solution is increased in accordance with the concentration elevation of the excrement, whereby in the pH adjustment step, the organic acid in the inactivation aqueous solution is subjected to concentration elevation by adjusting the inactivation aqueous solution to have a predetermined pH.

The present inventors have found that by adjusting the inactivation aqueous solution to have a predetermined pH, the superabsorbent polymers can be inactivated even if the concentration of excrement in the inactivation aqueous solution is elevated.

Next, in the above-mentioned invention, the organic acid can be recovered from the inactivation aqueous solution in which the organic acid is subjected to concentration elevation.

Therefore, the above-mentioned method can efficiently recover the organic acid which is included in the inactivation aqueous solution that includes excrement. In addition, after the recovery of the organic acid, the absolute amount of the inactivation aqueous solution to be treated can be reduced.

Aspect 2

The method according to aspect 1, wherein
in the pH adjustment step, the inactivation aqueous solution is adjusted to have the predetermined pH by adding an organic acid, removing a pH raising substance which raises pH, or a combination of the adding and the removing.

In the above-mentioned method, in the pH adjustment step, the inactivation aqueous solution is adjusted to have a predetermined pH by using predetermined means, whereby the inactivation aqueous solution can be easily adjusted to have a predetermined pH.

Aspect 3

The method according to aspect 2, wherein
the organic acid is an organic acid which includes a carboxyl group.

In the above-mentioned method, the organic acid is an organic acid which includes a carboxyl group, whereby it is difficult to damage the facility which inactivates the superabsorbent polymers, the facility which recovers the organic acid, etc.

Aspect 4

The method according to any one of aspects 1 to 3, wherein
the concentration elevation step further includes a sterilization step of sterilizing the inactivation aqueous solution.

The inactivation aqueous solution which includes excrement tends to reproduce funguses which are present in the excrement, funguses which are present in the environment, etc., as time lapses and as the organic acid and the excrement are subjected to concentration elevation.

In the above-mentioned method, the concentration elevation step further includes the sterilization step, whereby the funguses in the inactivation aqueous solution can be suppressed to a predetermined amount.

Aspect 5

The method according to aspect 4, wherein
in the sterilization step, the inactivation aqueous solution is sterilized by using ozone, chlorine dioxide, hydrogen peroxide, ultraviolet light, radiation, or any combination thereof.

In the above-mentioned method, in the sterilization step, the inactivation aqueous solution is sterilized by using a predetermined sterilization means, whereby the funguses in the inactivation aqueous solution can be suppressed to a predetermined amount, and the inactivation aqueous solution can be decolorized and deodorized. Further, in the above-mentioned method, the predetermined sterilization means is a sterilization means which does not substantially remain in the inactivation aqueous solution, whereby it is difficult for the sterilization means to remain in the organic acid aqueous solution to be recovered, and a step of separating the sterilization means becomes unnecessary.

Aspect 6

The method according to aspect 4 or 5, wherein
in the sterilization step, the inactivation aqueous solution is sterilized by using the ozone and deep ultraviolet light.

In the above-mentioned method, in the sterilization step, the inactivation aqueous solution is sterilized by using ozone and deep ultraviolet light, whereby bacteria, protozoa, (for example, cryptosporidium), etc., can be quickly deactivated.

Aspect 7

A method of producing recycled pulp fibers from a used absorbent article while elevating a concentration of and recovering an organic acid which inactivates superabsorbent polymers, the method comprising:

an inactivation step of inactivating the superabsorbent polymers by immersing a material which includes pulp fibers and superabsorbent polymers derived from the used absorbent article in an inactivation aqueous solution which has a predetermined pH and includes an organic acid;
a material extraction step of extracting the material from the inactivation aqueous solution which has been subjected to the inactivation step;
a recycled pulp fiber formation step of forming the recycled pulp fibers from the material which has been subjected to the material extraction step;
a pH adjustment step of adjusting the inactivation aqueous solution which has been subjected to the material extraction step to have a predetermined pH;
a concentration elevation step of elevating a concentration of the organic acid included in the inactivation aqueous solution by repeating the inactivation step which uses the inactivation aqueous solution that has been subjected to the pH adjustment step, the material extraction step, and the pH adjustment step; and
an organic acid recovery step of recovering the organic acid from the inactivation aqueous solution which has been subjected to the concentration elevation step.

The above-mentioned method can produce recycled pulp fibers while efficiently recovering the organic acid which is included in the inactivation aqueous solution that includes excrement.

Aspect 8

The method according to aspect 7, wherein
in the pH adjustment step, the inactivation aqueous solution is adjusted to have the predetermined pH by adding an organic acid, removing a pH raising substance which raises pH, or a combination of the adding and the removing.

In the above-mentioned method, in the pH adjustment step, the inactivation aqueous solution is adjusted to have a predetermined pH by using a predetermined means, whereby the inactivation aqueous solution can be easily adjusted to have a predetermined pH so as to efficiently produce recycled pulp fibers.

Aspect 9

The method according to aspect 8, wherein the organic acid is an organic acid which includes a carboxyl group.

In the above-mentioned method, the organic acid is an organic acid which has a carboxyl group, whereby it is difficult to damage the facility which inactivates the superabsorbent polymers, the facility which recovers the organic acid, etc.

Aspect 10

The method according to any one of aspects 7 to 9, wherein
the concentration elevation step further includes a sterilization step of sterilizing the inactivation aqueous solution.

In the above-mentioned method, the concentration elevation step further includes the sterilization step, whereby the funguses in the inactivation aqueous solution can be suppressed to a predetermined amount.

Aspect 11

The method according to aspect 10, wherein
in the sterilization step, the inactivation aqueous solution is sterilized by using ozone, chlorine dioxide, hydrogen peroxide, ultraviolet light, radiation, or any combination thereof.

In the above-mentioned method, in the sterilization step, the inactivation aqueous solution is sterilized by using a predetermined sterilization means, whereby the funguses in the inactivation aqueous solution can be suppressed to a predetermined amount, and the inactivation aqueous solution can be decolorized and deodorized. Further, in the above-mentioned method, the predetermined sterilization means is a sterilization means which does not substantially remain in the inactivation aqueous solution, whereby it is difficult for the sterilization means to remain in the organic acid aqueous solution to be recovered, and a step of separating the sterilization means becomes unnecessary.

Aspect 12

The method according to aspect 10 or 11, wherein
in the sterilization step, the inactivation aqueous solution is sterilized by using the ozone and deep ultraviolet light.

In the above-mentioned method, in the sterilization step, the inactivation aqueous solution is sterilized by using ozone and deep ultraviolet light, whereby bacteria, protozoa (for example, cryptosporidium), etc., can be quickly deactivated, and a reassuring and safe recycled pulp fibers can be produced.

Hereinbelow, a method of recovering an organic acid which inactivates superabsorbent polymers included in a used absorbent article of the present disclosure (hereinafter, which may be referred to as "a method of recovering an organic acid"), and a method of producing recycled pulp fibers from a used absorbent article while elevating a concentration of and recovering an organic acid which inactivates superabsorbent polymers (hereinafter, which may be referred to as "a method of producing recycled pulp") will be described in detail.

Method of Recovering an Organic Acid

The method of recovering an organic acid of the present disclosure includes the following steps.

(A1) an inactivation step of inactivating the superabsorbent polymers by immersing the superabsorbent polymers in an inactivation aqueous solution which has a predetermined pH and includes an organic acid (hereinafter, which may be referred to as "an inactivation step")

(A2) a superabsorbent polymer removal step of removing inactivated superabsorbent polymers from the inactivation aqueous solution which has been subjected to the inactivation step (hereinafter which may be referred to as "a superabsorbent polymer removal step")

(A3) a pH adjustment step of adjusting the inactivation aqueous solution which has been subjected to the superabsorbent polymer removal step to have a predetermined pH (hereinafter which may be referred to as "a pH adjustment step")

(A4) a concentration elevation step of elevating a concentration of the organic acid included in the inactivation aqueous solution by repeating the inactivation step which uses the inactivation aqueous solution that has been subjected to the pH adjustment step, the superabsorbent polymer removal step, and the pH adjustment step (hereinafter, which may be referred to as "a concentration elevation step")

(A5) an organic acid recovery step of recovering the organic acid from the inactivation aqueous solution which has been subjected to the concentration elevation step (hereinafter which may be referred to as "an organic acid recovery step")

The method of recovering an organic acid of the present disclosure may further include the following additional step.

(A6) a sterilization step of sterilizing the inactivation aqueous solution, in the concentration elevation step (hereinafter, which may be referred to as "a sterilization step")

FIG. 1 is a flow chart for explaining the method of recovering an organic acid of the present disclosure.

Inactivation Step S1

In the inactivation step S1, the superabsorbent polymers are immersed in an inactivation aqueous solution which has a predetermined pH and includes an organic acid so as to inactivate the superabsorbent polymers.

The organic acid is not particularly limited as long as the inactivation aqueous solution can be adjusted to a predetermined pH capable of inactivating the superabsorbent polymers, and examples of the organic acid include those having an acid group, for example, a carboxyl group, a sulfo group, etc. Incidentally, the organic acid having a sulfo group is referred to as a sulfonic acid, and the organic acid having a carboxyl group and not having a sulfo group is referred to as a carboxylic acid. The organic acid is preferably an organic acid having a carboxyl group, in particular, a carboxylic acid, from the viewpoint of carrying out the method of recovering an organic acid of the present disclosure, in particular, from the viewpoint of expanding the choices of an acid capable of generating a free organic acid and a water-insoluble salt in the organic acid generation step.

When the organic acid has a carboxyl group, the organic acid can have one or a plurality of carboxyl groups per molecule, and preferably has a plurality of carboxyl groups. This makes it easier for the organic acid to form a chelate complex with a divalent or higher metal, for example, calcium, which is included in the excrement, etc., and to lower the ash content of the recycled pulp fibers to be produced from the used absorbent article.

Examples of the organic acid include citric acid, tartaric acid, malic acid, succinic acid, oxalic acid (which are carboxylic acids having a plurality of carboxyl groups), gluconic acid ($C_6$), pentanoic acid ($C_5$), hutanoic acid ($C_4$), propionic acid ($C_3$), glycolic acid ($C_2$), acetic acid ($C_2$), formic acid ($C_1$) (which are carboxylic acids having a single carboxyl group), methanesulfonic acid, trifluoromethanesulfonic acid, benzenesulfonic acid, p-toluenesulfonic acid (which are sulfonic acids).

The predetermined pH is preferably 4.5 or less, more preferably 4.0 or less, still more preferably 3.5 or less, and even more preferably 3.0 or less. If the predetermined pH is too high, inactivation of the superabsorbent polymers may be insufficient.

Further, the predetermined pH is preferably 0.5 or more, and more preferably 1.0 or more. If the predetermined pH is too low, the recycled pulp fibers may be damaged, for example, when producing recycled pulp fibers from pulp fibers, as well as inactivating and removing the superabsorbent polymers from materials including pulp fibers and superabsorbent polymers.

In the inactivation step S1, the superabsorbent polymers can be inactivated by, for example, stirring the material which includes the pulp fibers and the superabsorbent polymers at a room temperature for approximately 5 to 60 minutes in an inactivation tank which includes the above-mentioned inactivation aqueous solution.

The above-mentioned superabsorbent polymers are not particularly limited as long as they are used as superabsorbent polymers in the art, and for example, those which have an acid group, for example, a carboxyl group, a sulfo group, etc., may be mentioned, and those which have a carboxyl group are preferable.

As the superabsorbent polymers which have a carboxyl group, for example, polyacrylate-based polymers and polyanhydrous maleate-based polymers may be mentioned, and as the superabsorbent polymers which have a sulfo group, etc., polysulfonate-based polymers may be mentioned.

Superabsorbent Polymer Removal Step S2

In the superabsorbent polymer removal step S2, the inactivated superabsorbent polymers are removed from the inactivation aqueous solution which has been subjected to the inactivation step S1. The inactivated superabsorbent polymers can be removed from the inactivated aqueous solution which has been subjected to the inactivation step by using, for example, a filter, etc.

pH Adjustment Step S3

In the pH adjustment step S3, the inactivation aqueous solution which has been subjected to the superabsorbent polymer removal step S2 is adjusted to have a predetermined pH.

Since the excrement usually includes a basic component such as ammonia, the pH of the inactivation aqueous solution tends to increase when the superabsorbent polymer is inactivated in the inactivation aqueous solution and the excrement is released into the inactivation aqueous solution. Therefore, it is preferable to adjust the inactivation aqueous solution to have a predetermined pH.

The predetermined pH is preferably 4.5 or less, more preferably 4.0 or less, still more preferably 3.5 or less, and even more preferably 3.0 or less. If the predetermined pH is too high, the inactivation of the superabsorbent polymer may be insufficient.

The predetermined pH is preferably 0.5 or more, and more preferably 1.0 or more. If the predetermined pH is too low, the recycled pulp fibers may be damaged, for example, when producing recycled pulp fibers from pulp fibers, as well as inactivating and removing the superabsorbent polymers from materials including pulp fibers and superabsorbent polymers.

In the pH adjustment step S3, the inactivation aqueous solution can be adjusted to have a predetermined pH by adding an organic acid to the inactivation aqueous solution.

Further, the pH adjustment step S3 can adjust the inactivation aqueous solution to have a predetermined pH by removing a pH raising substance that raises pH from the inactivation aqueous solution. As examples of the pH raising substance, for example, basic components such as sodium and ammonia, etc., may be mentioned, and as the means of removing the pH raising substance, electrodialysis may be mentioned.

As the electrodialysis device which performs the electrodialysis, one in which a cation exchange membrane which can permeate sodium ions ($Na^+$), ammonium ions $NH_4^+$), etc., and an anion exchange membrane which cannot permeate citrate ions are alternately arranged between a pair of electrodes may be mentioned. For example, an inactivation aqueous solution may be passed through the above-mentioned electrodialysis device so as to be separated into a concentrated solution in which sodium ions ($Na^+$), ammonium ions ($NH_4^+$), etc., are concentrated, and a desalting solution in which citric acid remains, and the desalting solution may be regarded as the inactivation aqueous solution.

As the electrodialysis device which performs the electrodialysis, one in which a cation exchange membrane and an anion exchange membrane which can permeate citrate ions are alternately arranged between a pair of electrodes may be mentioned. For example, the above-mentioned desalting solution may be passed through the above-mentioned electrodialysis device so as to be separated into a concentrated solution in which citrate ions are concentrated and a desalting solution, and the concentrated solution may be regarded as an inactivation aqueous solution.

Concentration Elevation Step S4

In the concentration elevation step S4, the cycle of the inactivation step S1 which uses the inactivation aqueous solution that has been subjected to the pH adjustment step S3, the superabsorbent polymer removal step S2, and the pH adjustment step S3 is repeated so as to elevate the concentration of the organic acid in the inactivation aqueous solution.

In the concentration elevation step S4, in particular, by repeating the inactivation step S1, the excrement retained by the superabsorbent polymers is repeatedly released into the inactivation aqueous solution, whereby elevates the concentration of the excrement in the inactivation aqueous solution. Further, since the pH of the inactivation aqueous solution elevates in accordance with the concentration elevation of the excrement, in the pH adjustment step S3, when the organic acid is added so as to adjust the inactivation aqueous solution to have a predetermined pH, the concentration of the organic acid in the inactivation aqueous solution elevates.

Incidentally, in the superabsorbent polymer removal step S2 in the concentration elevation step S4, when the inactivated superabsorbent polymers are removed, a portion of the inactivation aqueous solution may be removed together with the superabsorbent polymers. In such a case, in the inactivation step S1 in the concentration elevation step S4, a new organic acid, water, etc., may be supplemented to the inactivation aqueous solution obtained in the pH adjustment step S3 so as to adjust the amount of the inactivation aqueous solution.

Sterilization Step S5

The sterilization step S5 is not an essential step of the recovery method of the present disclosure, and is an optional step if desired. The inactivation aqueous solution which includes the excrement tends to reproduce funguses which are present in the excrement, funguses which are present in the environment, etc., as time lapses and as the organic acid and the excrement are subjected to concentration elevation. The sterilization step S5 can be performed by using sterilization means known in the art, and as the sterilization means, for example, sterilizing agents, ozone, chlorine dioxide, hydrogen peroxide, ultraviolet light and radiation, the combination of the aforementioned may be mentioned.

As the ultraviolet light, for example, deep ultraviolet light having a wavelength of 210 to 350 nm may be mentioned. In the sterilization step S5, bacteria, protozoa, example, cryptosporidium), etc., can be deactivated by using deep ultraviolet light.

As the radiation, electromagnetic radiation (X-rays and γ-rays), particle beams (β-rays, electron beams, proton beams, deuteron beams, α-rays, and neutron beams), etc., may be mentioned.

As the above combination, a combination of ozone and ultraviolet light, in particular, a combination of ozone and deep ultraviolet light is preferable. By this combination, not only funguses but also viruses, bacteria, protozoa (for example, cryptosporidium), etc., can be quickly deactivated without the concentration elevation of ozone and performing the treatment with ozone for a long time, as compared with the case where the sterilization step S5 is performed only with ozone. Incidentally, h the concentration elevation of ozone and by performing the treatment with ozone for a long time, corrosion of equipment by ozone, necessity of deozonating the inactivation aqueous solution, etc., may occur.

The sterilization step S5 can sterilize the inactivation aqueous solution so that the number of general bacteria is preferably 100 bacteria/mL or less, more preferably 50 bacteria/mL or less, and even more preferably 20 bacteria/mL or less.

Incidentally, the quantity of general bacteria is measured according to HS K0350-10-10:2002 "Test Methods for General Bacteria in Water and Waste Water".

The sterilizing means is preferably a sterilizing means which does not substantially remain in the inactivation aqueous solution after the sterilization step S5. This is for the purpose of not letting the sterilizing means remain in the organic acid aqueous solution from which the organic acid is to be recovered. Further, in the inactivation step S1, when the superabsorbent polymers in the material which includes the superabsorbent polymers and the pulp fibers are inactivated and the recycled pulp fibers are produced, there is a possibility that the sterilization means remains in the recycled pulp fibers, and necessity of removing the sterilization means from the recycled pulp fibers may occur.

As the sterilizing means that do not substantially remain in the inactivation aqueous solution, sterilizing agents, ozone, chlorine dioxide, hydrogen peroxide, ultraviolet light and radiation, and the combination of the aforementioned may be mentioned.

The concentration elevation step S4 may further include a decolorizing step of decolorizing the inactivation aqueous solution by using a decolorizing means, a deodorizing step of deodorizing the inactivation aqueous solution by using a deodorizing means, etc. This is because the above-mentioned inactivation aqueous solution tends to cause coloration, odor, etc., derived from the excrement as the concentration of the excrement elevates.

The decolorizing means is preferably a decolorizing means which does not substantially remain in the inactivation aqueous solution after the decolorizing step. The deodorizing means is preferably a deodorizing means which does not substantially remain in the inactivation aqueous solution after the deodorizing step. Further, it is preferable that the sterilizing means also serves as a decolorizing means and a deodorizing means.

As a sterilizing means which also serves as a decolorizing means and a deodorizing means, in particular a sterilizing means (a decolorizing means and a deodorizing means) which is capable of sterilizing, decolorizing and deodorizing, and which substantially does not remain in the inactivation aqueous solution after the sterilization step S5, ozone, chlorine dioxide, hydrogen peroxide, ultraviolet light and radiation, and any combination of the aforementioned may be mentioned.

Incidentally, the sterilization step S5 can be performed at any position in the concentration elevation step S4, for example, before the pH adjustment step S3 and/or after the pH adjustment step S3. In addition, the sterilization step S5 can be performed once per cycle of the inactivation step S1, the superabsorbent polymer removal step S2, and the pH adjustment step S3, and for example, can be performed once per five cycles, as appropriate depending on, for example, the amount of funguses, the degree of coloration, the degree of odor, etc., of the inactivation aqueous solution.

Incidentally, in FIG. 1, as an example, the sterilization step S5 is arranged before and after the pH adjustment step S3.

The concentration elevation step S4 can be carried out until the concentration of the organic acid in the inactivation aqueous solution is finally 1.5 to 10.0% by mass, more preferably 2.0 to 8.0% by mass, and even more preferably 2.3 to 6.0% by mass. By doing so, in the inactivation step S1, it is possible to efficiently recover the organic acid while suppressing the inhibition of the inactivation of the superabsorbent polymers and the precipitation of the organic acid in the inactivation aqueous solution.

Incidentally, in the inactivation aqueous solution after having been subjected to the concentration elevation step S4, the concentration of the organic acid and the excrement is elevated.

Organic Acid Recovery Step S6

In the organic acid recovery step S6, the organic acid is recovered from the inactivation aqueous solution which has been subjected to the concentration elevation step S4.

The organic acid recovery step SC can recover the organic acid from the inactivation aqueous solution which has been subjected to the inactivation step S1, the superabsorbent polymer removal step S2 or the pH adjustment step S3, or the sterilization step S5, within the concentration elevation step S4, and it is preferable to recover the organic acid from the inactivation aqueous solution which has been subjected to the superabsorbent polymer removal step S2 or the sterilization step S5. This is because the inactivation aqueous solution which has been subjected to the inactivation step S1 includes inactivated superabsorbent polymers, which are not suitable for the recovery of the organic acid, and as for the inactivation aqueous solution which has been subjected to the pH adjustment step S3, the pH adjustment step S3 itself becomes meaningless.

The organic acid recovery step S6 can employ a method known in the art without particular limitation, and the organic acid can be purified by, for example, electrodialysis.

Further, when not only the organic acid but also the excrement is recovered from the inactivation aqueous solution, for example, the organic acid recovery step S6 can be performed by the following recovery method of the organic acid and the excrement.

(B1) a precipitation step of precipitating a water-insoluble salt of an organic acid by adding a metal salt which includes a divalent or higher metal or a base which includes a divalent or higher metal (hereinafter, which may be referred to as "a precipitation step")

(B2) a mixture collection step of collecting a mixture of the water-insoluble salt of an organic acid and solid excrement derived from the excrement, from the inactivation aqueous solution which has been subjected the precipitation step (hereinafter, which may be referred to as "a mixture collection step")

(B3) an organic acid generation step of forming an aqueous solution which includes an organic acid, the water-insoluble salt and solid excrement by adding an acid capable of generating a free organic acid and a water-insoluble salt (hereinafter which may be referred to as "a free organic acid generating acid") and water to the mixture (hereinafter, Which may be referred to as "an organic acid generation step").

(B4) an organic acid solution obtainment step of obtaining an organic acid aqueous solution which includes an organic acid by removing the water-insoluble salt and the solid excrement from the above-mentioned aqueous solution (hereinafter, which may be referred to as "an organic acid solution obtainment step")

Figure 2:
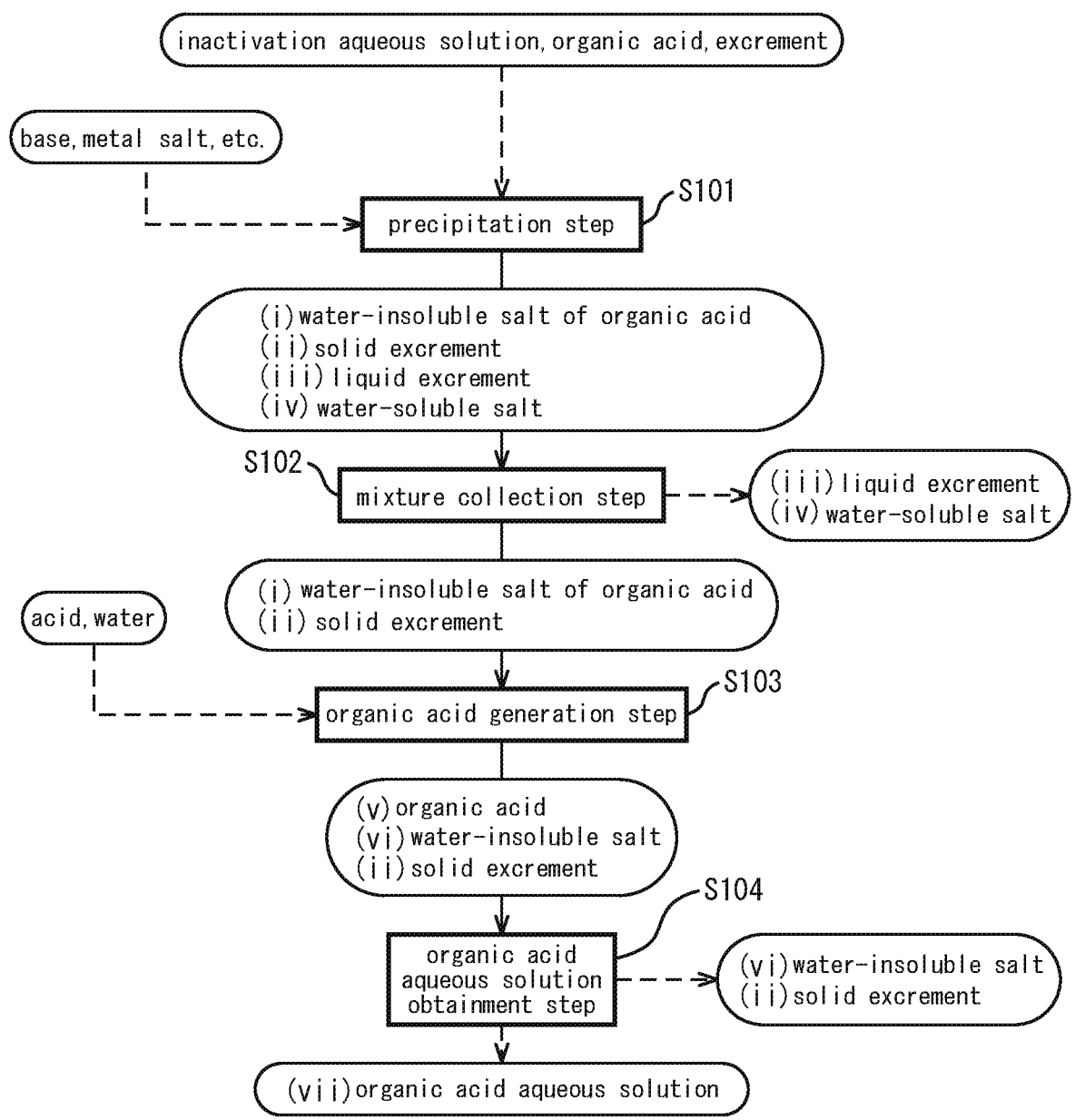
FIG. 2 is a flow chart for explaining the method of recovering an organic acid and excrement.

Further, FIG. 2 is a flow chart for explaining the method of recovering an organic acid and excrement.

Precipitation Step S101

In the precipitation step S101, a metal salt which includes a divalent or higher metal or a base which includes a divalent or higher metal (hereinafter, which may be referred to as "a water-insoluble salt generating salt") is added to the inactivation aqueous solution for superabsorbent polymers which includes excrement and an organic acid so as to precipitate a. water-insoluble salt of the organic acid. Specifically, in the precipitation step S101, a metal salt which includes a divalent or higher metal or a base which includes a divalent or higher metal is added to the inactivation aqueous solution so as to obtain an inactivation aqueous solution which includes (i) a water-insoluble salt of an organic acid, and excrement [(ii) solid excrement and (iii) liquid excrement], and (iv) an aqueous solution salt.

In an inactivation aqueous solution for a superabsorbent polymers which includes excrement and organic acid, excrement, etc., such as organic acid, feces, urine, and the like is present. Organic acids are predominantly dissolved in the inactivation aqueous solution, and among the above-mentioned excrement, (iii) liquid excrement such as urine, in a liquid state, is predominantly dissolved in the inactivation aqueous solution, and (ii) solid excrement such as feces, in a solid state, is predominantly dispersed in the inactivation aqueous solution.

In the precipitation step S101, by adding a metal salt which includes a divalent or higher metal (hereinafter, which may be simply referred to as "a metal salt") to the inactivation aqueous solution, (i) when a water-insoluble salt of an organic acid is precipitated, the inactivation aqueous solution may not be neutralized or may be neutralized before the addition of the metal salt, however, it is preferable to add a base for neutralization (hereinafter, which may be referred to as a "neutralizing base") to the inactivation aqueous solution before the addition of the metal salt so as to neutralize the inactivation aqueous solution. This makes it difficult for the organic acid to form a chelate complex with the metal, whereby improving the recovery of the organic acid. The technique of adding a metal salt after neutralization is particularly useful when the organic acid is an organic acid capable of forming a chelate complex with a metal.

In this description, the base (neutralizing base and water-insoluble salt generating base) is preferably a base based on the definition of a Brønsted-Lowry, i.e., a material capable of receiving a proton $H^+$.

Incidentally, when the organic acid is an organic acid capable of forming a chelate complex with a metal, the neutralizing base is preferably a base which includes a monovalent metal, for example, lithium hydroxide, sodium hydroxide, or potassium hydroxide. This is to suppress the organic acid from forming a chelate complex.

The inactivation aqueous solution for superabsorbent polymers, including excrement and an organic acid, can be neutralized to a pH of preferably 5.0 to 10.0, more preferably 6.0 to 9.0, and even more preferably 6.5 to 8.0, by the addition of a neutralizing base. By doing so, when the organic acid is an organic acid capable of forming a chelate complex with a metal, it is possible to suppress the organic acid from forming a chelate complex.

The metal salt is not particularly limited as long as it can react with an organic acid to generate (i) a water-insoluble salt of an organic acid and (iv) a water-soluble salt.

It is preferable that the above-mentioned metal salt has a solubility classified as "being extremely easy to dissolve", "being easy to dissolve", "being relatively easy to dissolve", or "being relatively difficult to dissolve" in "General Rule 29" of the "Japanese Pharmacopoeia, 15th revision". This is from the viewpoints of shortening the reaction time with the organic acid and (i) making it difficult for unreacted metal salt to remain in the water-insoluble salt of the organic acid.

The metal salt is preferably a salt of an acid and a base which includes a divalent or higher metal.

When a metal salt is added after neutralization of the inactivation aqueous solution, it is preferable that the divalent or higher metals constituting the metal salt have an ionization tendency close to that of the metal constituting the neutralizing base. By doing so, the organic acid in the inactivation aqueous solution can be converted into (i) a water-insole e salt of the organic acid in high yield.

The acid which can constitute the metal salt is preferably water-soluble, can be an organic acid or an inorganic acid, and is preferably an inorganic acid. This is from the viewpoint of recovery of the organic acid. As the inorganic acid, hydrochloric acid, sulfuric acid, nitric acid, iodic acid, bromic acid, etc., may be mentioned.

As the divalent or higher metals constituting the metal salt, for example, the group consisting of Mg, Ca, Ba, Fe, Ni, Cu, Zn, and Al, and any combination thereof, may be mentioned. When the metal salt is composed of a divalent or higher metal, (i) it is easier for a water-insoluble salt of an organic acid (composed of an organic acid and a divalent or higher metal) to precipitate in an inactivation aqueous solution, and in a subsequent mixture collection step, (i) it is easier for a water-insoluble salt of an organic acid tends to be collected.

The metal salt is preferably added in an amount such that it is 0.8 times equivalent or more, more preferably 0.9 times equivalent or more, and even more preferably 1.0 times equivalent or more, with respect to the organic acid. Further, the metal salt is preferably added in an amount of 3.0 times equivalent or less, more preferably 2.5 times equivalent or less, and even more preferably 2.0 times equivalent or less, with respect to the organic acid. (i) This is from the viewpoint of forming a water-insoluble salt of an organic acid.

The equivalent amount means an equivalent amount of the valence of the metal constituting the metal salt to the number of acid groups constituting the organic acid.

In order to determine the addition amount of the metal salt, it is preferable to grasp the amount of the organic acid in the inactivation aqueous solution. The amount of organic acid in the inactivation aqueous solution may be ascertained by directly measuring the concentration of the organic acid in the inactivation aqueous solution to which the metal salt is added, and may also be ascertained by subtracting the amount of inactivation aqueous solution discharged together with the superabsorbent polymers, pulp fibers, etc. (the amount of discharged organic acid) from the total amount (history) of organic acid added to the inactivation aqueous solution.

Further, when the amount of the organic acid in the inactivation aqueous solution is unknown, etc., a metal salt which is considered to be an excess amount with respect to the organic acid may be added, and the excess metal salt may be separated from the organic acid aqueous solution in a subsequent mixture collection step, organic acid solution obtainment step, etc.

When the organic acid is an organic acid having a carboxyl group, the acid may be, for example, hydrochloric acid, sulfuric acid, nitric acid, etc.

Further, when the organic acid is an organic acid which does not form a chelating complex with a metal, (i) the water-insoluble salt of the organic acid can be precipitated by adding a water-insoluble salt generating base which includes a divalent or higher metal to the inactivation aqueous solution without neutralizing the inactivation aqueous solution in the precipitation step S101. By doing so, the organic acid and the excrement can be recovered from the inactivation aqueous solution which includes the organic acid and excrement, respectively, in a small number of steps.

As the divalent or higher metals constituting the water-insoluble salt generating base, for example, the group consisting of Mg, Ca, Ba, Fe, Ni, Cu, Zn, and Al, and any combination thereof may be mentioned.

As examples of the water-insoluble salt generating base, magnesium hydroxide, calcium hydroxide, copper hydroxide, and zinc hydroxide, etc., may be mentioned.

The water-insoluble salt generating base is preferably added in an amount such that it is 0.8 times equivalent or more, more preferably 0.9 times equivalent or more, and even more preferably 1.0 times equivalent or more with respect to the organic acid. Further, the water-insoluble salt generating base is preferably added in an amount such that it is 3.0 times equivalent or less, more preferably 2.5 times equivalent or less, and still more preferably 2.0 times equivalent or less with respect to the organic acid. (i) This is from the viewpoint of forming a water-insoluble salt of an organic acid.

The equivalent amount means an equivalent amount of the valence of the divalent or higher metal constituting the water-insoluble salt generating base to the number of acid groups constituting the organic acid.

As examples of organic acids that do not form chelating complexes with metals, pentanoic acid ($C_5$), butanoic acid ($C_4$), propionic acid ($C_3$), acetic acid ($C_2$), formic acid ($C_1$), etc., may be mentioned.

As examples of the organic acid capable of forming a chelate complex with a metal, citric acid, oxalic acid, tartaric acid, and gluconic acid, etc., may be mentioned.

In the precipitation step S101, (i) a water-insoluble salt of the organic acid is formed, the salt crystallizes and precipitates. At this time, (ii) fine components among the solid excrement dispersed in the inactivation aqueous solution, (i) adheres to the surface of the water-insoluble salt of the organic acid, and (i) is incorporated into the crystals of the water-insoluble salt of the organic acid and aggregates. Accordingly, in the mixture collection step S102, fine (ii) solid excrement is collected as solids (i.e., (i) water-insoluble salt of an organic acid and (ii) solid excrement) and is less likely to be included in liquids (i.e., (iii) liquid excrement and (iv) water-soluble salt). As a result, the concentration of the floating matter SS in the liquid is lowered, clogging of a filter, etc., is hardly caused during the solid-liquid separation for separating the liquid and the solid, and the amount of sludge generated during the microbial treatment of the liquid is reduced.

The inactivation aqueous solution that has been subjected to the precipitation step S101 includes (i) water-insoluble salts of organic acids, (ii) solid excrement, (iii) liquid excrement, and (iv) water-soluble salts.

Mixture Collection Step S102

In the mixture collection step S102, a mixture of water-insoluble salts of organic acids and solid excrement is collected from the inactivation aqueous solution that has been subjected to the precipitation step S101.

Specifically, the mixture collection step S102 separates the inactivation aqueous solution which includes (i) a water-insoluble salt of an organic acid, (ii) a solid excrement, (iii) a liquid excrement, and (iv) a water-soluble salt into a solid [i.e., (i) a water-insoluble salt of an organic acid and (ii) a solid excrement], and a liquid [i.e., (iii) a liquid excrement and (iv) a water-soluble salt].

Organic Acid Generation Step S103

In the organic acid generation step S103, an acid capable of generating an organic acid and a water-insoluble salt, and water are added to the mixture so as to form an aqueous solution which includes the organic acid and the water-insoluble salt and solid excrement. Specifically, in the organic acid generation step S103, free organic acid generating acid and water are added to a solid [i.e., (i) a water-insoluble salt of an organic acid and (ii) a solid excrement], so that (v) an organic acid, (vi) a water-insoluble salt, and (ii) an aqueous solution which includes the solid excrement are formed.

The free organic acid generating acid is not particularly limited as long as it is (i) an acid which can free the organic acid from the water-insoluble salt of the organic acid and generate the water-insoluble salt, however, one having an acid dissociation constant ($pK_a$, in water) smaller than the acid dissociation constant ($pK_a$, in water) of the organic acid is preferable.

Incidentally, when the organic acid has a plurality of acid groups, for example, when the organic acid is a dibasic acid or a tribasic acid, it is preferable that the free organic acid generating acid has an acid dissociation constant ($pK_a$, in water) smaller than the smallest acid dissociation constant ($pK_a$, in water) among the acid dissociation constants ($pK_a$, in water) of the organic acid. This is from the viewpoint of facilitating the formation of free organic acids.

Further, when the free organic acid generating acid has a plurality of acid groups, for example, when the free organic acid generating acid is a dibasic acid or a tribasic acid, it is preferable that the largest acid dissociation constant ($pK_a$, in water) among the acid dissociation constants ($pK_a$, in water) of the free organic acid generating acid is smaller than the smallest acid dissociation constant ($pK_a$, in water) among the acid dissociation constants ($pK_a$, in water) of the organic acid. This is from the viewpoint of the efficiency of the free organic acid generating acid.

The acid having an acid dissociation constant ($pK_a$, in water) smaller than the acid dissociation constant ($pK_a$, in water) of the organic acid can be an organic acid or an inorganic acid, and is preferably an inorganic acid. As examples of the inorganic acid, hydrochloric acid, sulfuric acid, nitric acid, iodic acid, bromic acid, etc., may be mentioned.

In the present description, the values set forth in the Electrochemical Manual, edited by the Electrochemical Society can be adopted as the acid dissociation constants ($pk_a$, in water)

According to the electrochemical handbook, the acid dissociation constants ($pk_a$, 25° C. in water) of the major compounds are as follows:

Organic Acid

Tartaric acid: 2.99 ($pK_{a1}$), 4.44 ($pK_{a2}$)
Malic acid: 3.24 ($pK_{a1}$), 4.71 ($pK_{a2}$)
Citric acid: 2.87 ($pK_{a1}$), 4.35 ($pK_{a2}$), 5.69 ($pK_{a3}$)

Inorganic Acid

Sulfuric acid: 1.99

The acid dissociation constants ($pk_a$, in water) of acids not listed in the electrochemical handbook can be determined by measurements. As an instrument capable of measuring the acid dissociation constants of acid ($pk_a$, in water), for example, a compound property evaluation analysis system, T3, manufactured by Sirius Corporation, may be mentioned.

The free organic acid generating acid is preferably added in an amount such that it is 0.8 times equivalent or more, more preferably 0.9 times equivalent or more, and even more preferably 1.0 times equivalent or more, with respect to the organic acid. (i) This is from the viewpoint of making the water-insoluble salt of the organic acid a (v) organic acid in the free state.

Further, the free organic acid generating acid is preferably added in an amount such that it is 3.0 equivalent or less, more preferably 2.5 equivalent or less, and even more preferably 2.0 equivalent or less with respect to the organic acid. (vii) This is from the viewpoint of making the free organic acid generating acid hardly remain in the organic acid aqueous solution to be recovered, and from the viewpoint of making the equipment hardly corrode, etc.

Incidentally, the equivalent amount means an equivalent amount of the number of acid groups of the free organic acid generating acid to the number of acid groups constituting the organic acid.

The adding amount of free organic acid forming acid can be determined based on (i) the composition of the water-insoluble salt of the organic acid, as well as the dry mass thereof.

Further, the free organic acid generating acid and water to be added in the organic acid generation step S103 may be added to the mixture separately, and may be added together to the mixture as an aqueous solution of the free organic acid generating acid.

Organic Acid Solution Obtainment Step S104

In the organic acid aqueous solution obtainment step S104, the water-insoluble salt and solid excrement are removed from the above-mentioned aqueous solution so as to obtain an organic acid aqueous solution which includes an organic acid. Specifically, in the organic acid aqueous solution obtainment step S104, solid matter, i.e., (vi) water-insoluble salt, and (ii) solid excrement are removed from the aqueous solution which includes (v) organic acid, (vi) water-insoluble salt, and (ii) solid excrement so as to obtain a liquid matter, i.e., (vii) organic acid aqueous solution which includes (v) organic acid.

Production Method of Recycled Pulp Fibers

The production method of recycled pulp fibers of the present disclosure includes the following steps.
(C1) an inactivation step of inactivating the superabsorbent polymers by immersing a material which includes pulp fibers and superabsorbent polymers derived from the used absorbent article in an inactivation aqueous solution which has a predetermined pH and includes an organic acid (hereinafter, which may be referred to as "an inactivation step")
(C2) a material extraction step of extracting the material from the inactivation aqueous solution which has been subjected to the inactivation step (hereinafter which may be referred to as "a material extraction step")
(C3) a recycled pulp fiber formation step of forming the recycled pulp fibers from the material which has been subjected to the material extraction step (hereinafter which may be referred to as "a recycled pulp fiber formation step")
(C4) a pH adjustment step of adjusting the inactivation aqueous solution which has been subjected to the material extraction step to have a predetermined pH (hereinafter which may be referred to as "a pH adjustment step")
(C5) a concentration elevation step of elevating the concentration of the organic acid included in the inactivation aqueous solution by repeating the inactivation step which uses the inactivation aqueous solution that has been subjected to the pH adjustment step, the material extraction step, and the pH adjustment step (hereinafter, which may be referred to as a "a concentration elevation step").
(C6) an organic acid recovery step of recovering the organic acid from the inactivation aqueous solution which has been subjected to the concentration elevation step (hereinafter, which may be referred to as the organic acid recovery step)

The production method of recycled pulp fibers of the present disclosure may further include the following additional step.
(C7) a sterilization step of sterilizing the inactivation aqueous solution in the concentration elevation step (hereinafter, which may be referred to as "a sterilization step")

Figure 3:
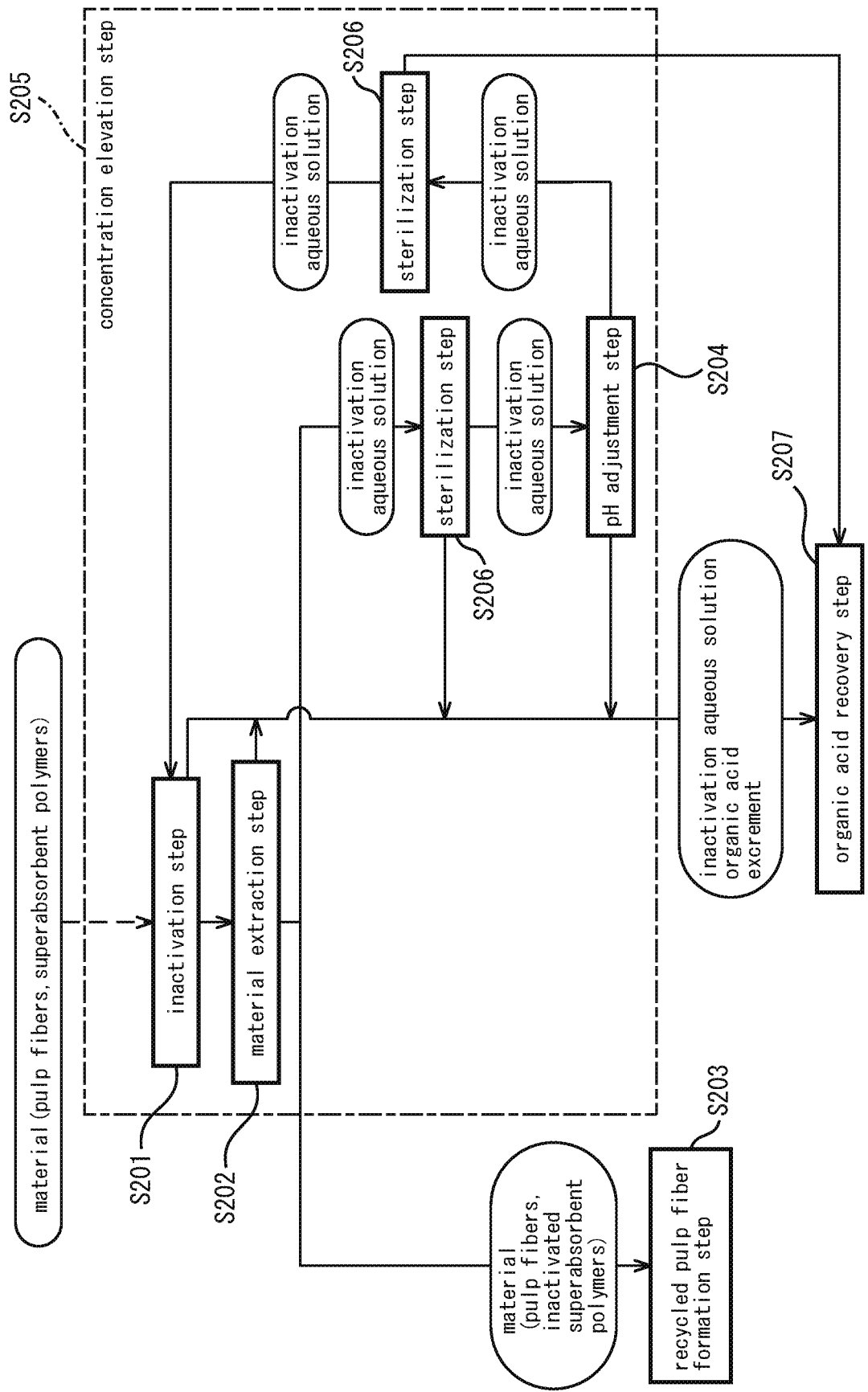
FIG. 3 is a flow chart which illustrates a method of producing recycled pulp fibers of the present disclosure.

FIG. 3 is a flow chart which illustrates the production method of recycled pulp fibers of the present disclosure.

Inactivation Step S201

In the inactivation step S201, a material which includes pulp fibers and superabsorbent polymers derived from a used absorbent article is immersed in an inactivation aqueous solution which has a predetermined pH and includes an organic acid so as to inactivate the superabsorbent polymers.

As the materials which includes pulp fibers and superabsorbent polymers derived from a used absorbent article, a material consisting of superabsorbent polymers and pulp fibers (e.g., absorbent cores), absorbent articles (e.g., crushed absorbent articles), etc., may be mentioned.

The predetermined pH is preferably 4.5 or less, more preferably 4.0 or less, still more preferably 3.5 or less, and even more preferably 3.0 or less. If the predetermined pH is too high, inactivation of the superabsorbent polymers may be insufficient.

Further, the predetermined pH is preferably 0.5 or more, and more preferably 1.0 or more. If the predetermined pH is too low, the recycled pulp fibers may be damaged, for example, when producing recycled pulp fibers from pulp fibers, as well as inactivating and removing the superabsorbent polymers from materials including pulp fibers and superabsorbent polymers.

Material Extraction Step S202

In the material extraction step S202, the material is extracted from the inactivation aqueous solution which has been subjected to the inactivation step. The material extraction step S202 can be performed by using, for example, a filter, etc.

Recycled Pulp Fiber Formation Step S203

In the recycled pulp fiber formation step S203, recycled pulp fibers are formed from the material that has been subjected to the inactivation step S201. The specific means of forming the recycled pulp fibers is not particularly limited and can be carried out by methods known in the art.

For example, as described in Patent Literature 1, by blowing ozone gas into an aqueous solution which includes material including pulp fibers and inactivated superabsorbent polymers (e.g., an inactivation aqueous solution), which has been subjected to an inactivation step S201, the inactivated superabsorbent polymers are solubilized, and the pulp fibers are sterilized, bleached, deodorized, etc., so as to form recycled pulp fibers.

The pH adjustment step S204, the concentration elevation step S205, the sterilization step S206, and the organic acid recovery step S207 are the same as the pH adjustment step S3, the concentration elevation step S4, the sterilization step S5, and the organic acid recovery step S6, respectively, in the organic acid recovery process of the present disclosure, and therefore the description thereof will be omitted.

Figure 4:
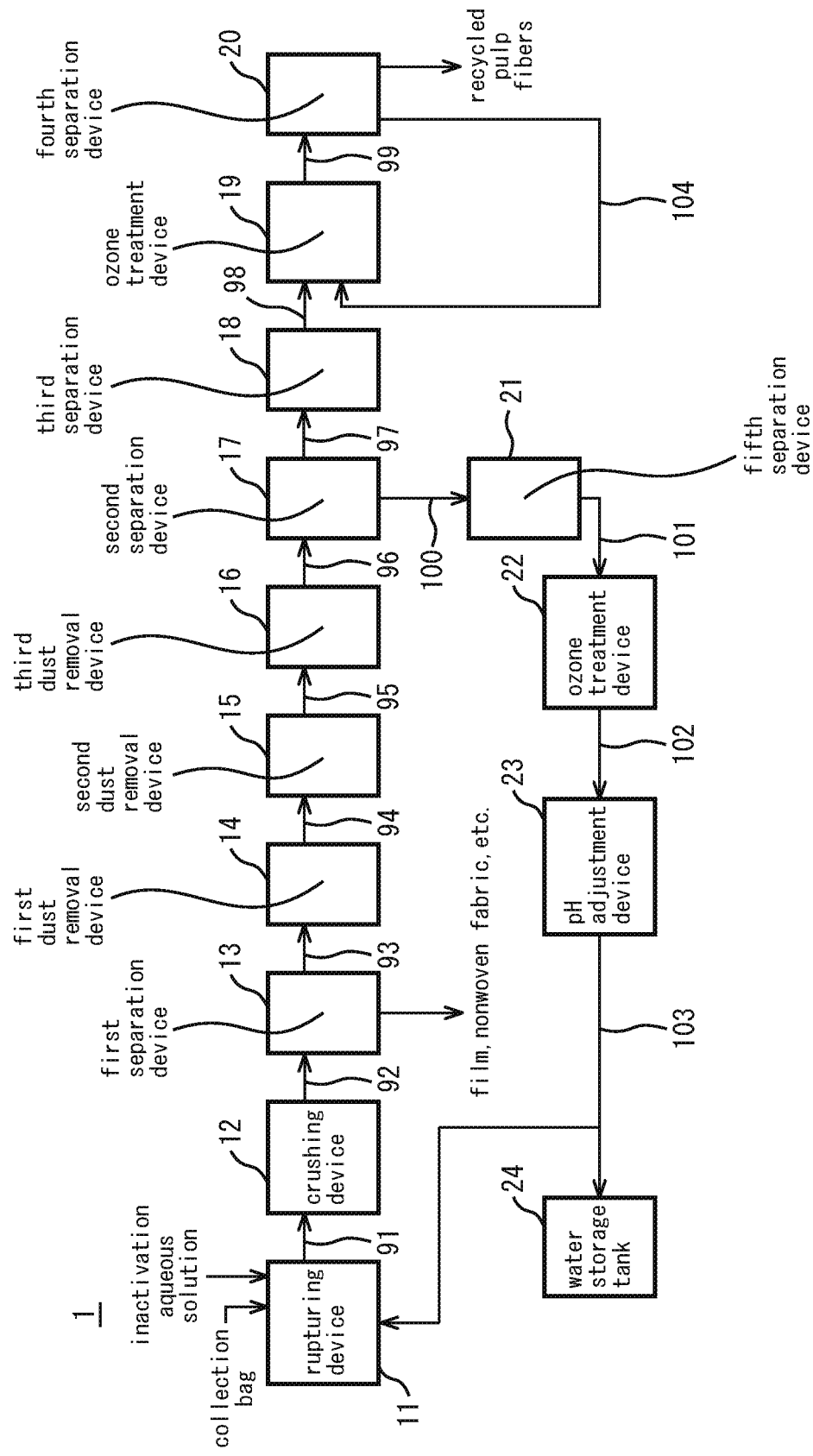
FIG. 4 is a block diagram which illustrates an example of a system 1 for implementing the present disclosure.

FIG. 4 is a block diagram which illustrates an example of a system 1 for implementing the present disclosure.

The system 1 includes a rupturing device 11, a crushing device 12, a first separation device 13, a first dust removal device 14, a second dust removal device 15, a third dust removal device 16, a second separation device 17, a third separation device 18, an ozone treatment device 19, a fourth separation device 20, a fifth separation device 21, an ozone treatment device 22, a pH adjustment device 23, and a water storage tank 24.

Figure 5:
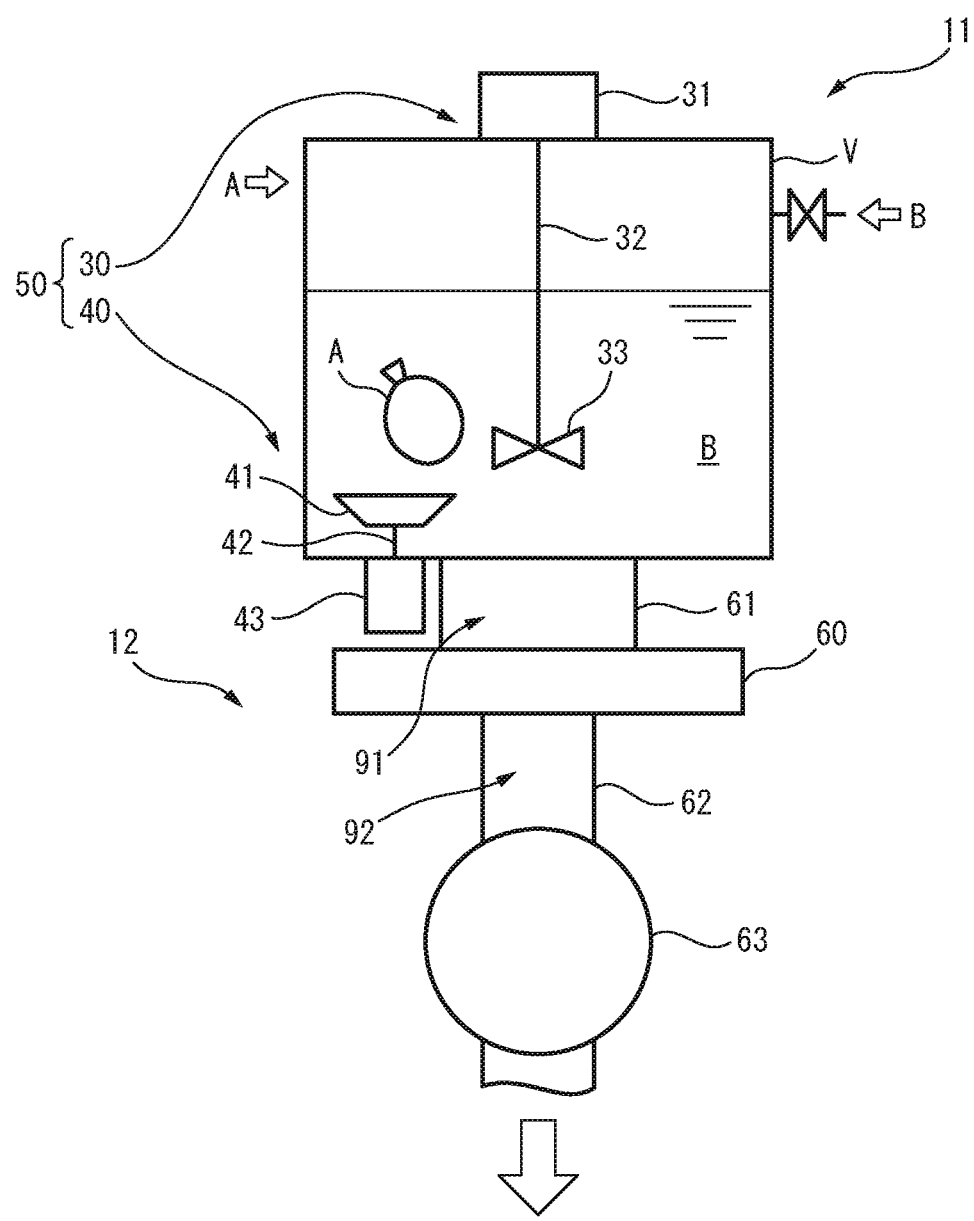
FIG. 5 is a schematic diagram which shows a configuration example of the rupturing device 11 and the crushing device 12 of FIG. 4.

The rupturing device 11 punctures a collection bag which includes used absorbent articles in an inactivation aqueous solution. The crushing device 12 crushes the used absorbent article in the inactivation aqueous solution sank below the surface of the inactivation aqueous solution together with the collection bag. FIG. 5 is a schematic diagram which shows a configuration example of the rupturing device 11 and the crushing device 12 of FIG. 4.

The rupturing device 11 is filled with an inactivation aqueous solution B, and a hole is formed in the collection bag A that has sunk in the inactivation aqueous solution B. The rupturing device 11 includes a solution tank V and a hole punching portion 50. The solution tank V stores the inactivation aqueous solution B. The hole punching portion 50 is provided in the solution tank V, and when the collection bag A is put into the solution tank V, the hole punching portion 50 punctures the surface of the collection bag A in contact with the inactivation aqueous solution B.

The hole punching portion 50 includes a feeding section 30 and a rupturing section 40. The feeding section 30 feeds (physically forces) the collection bag A into the inactivation aqueous solution B in the solution tank V. As the feeding section 30, for example, a stirrer may be mentioned, and includes a stirring blade 33, a supporting shaft (a rotation shaft) 32 supporting the stirring blade 33, and a driving device 31 rotating along the shaft of the supporting shaft 32. The stirring blade 33 rotates around the rotation shaft (supporting shaft) 32 by the driving device 31, whereby causing a swirling flow of the inactivation aqueous solution B. The feeding section 30 draws the collection bag A toward the bottom portion direction of the inactivation aqueous solution B (solution tank V) by the swirling flow.

The rupturing section 40 is disposed at the lower portion (preferably at the bottom portion) of the solution tank V, and includes a rupturing blade 41, a supporting shaft (a rotation shaft) 42 for supporting the rupturing bag blade 41, and a driving device 43 rotating along the shaft of the supporting shaft 42. The rupturing blade 41 is rotated around the rotation shaft (supporting shaft) 42 by the driving device 43, whereby making a hole in the collection bag A that has moved to the lower portion of the inactivation aqueous solution B (solution tank V).

The crushing device 12 crushes the used absorbent articles in the collection bag A which has sank under the water surface of the inactivation aqueous solution B together with the collection bag A. The crushing device 12 includes a crushing section 60 and a pump 63. The crushing section 60 is connected to the solution tank V by a pipe 61, and crushes the used absorbent article (mixed solution 91) in the collection bag A, which is delivered together with the inactivation aqueous solution B from the solution tank V, together with the collection bag A, in the inactivation aqueous solution B.

As examples of the crushing section 60, a biaxial crusher (for example, a biaxial rotary crusher, a biaxial differential crusher, and a biaxial shear crusher), may be mentioned, and for example, a SUMICUTTER (manufactured by Sumitomo Heavy Industries Environment Co., Ltd.). The pump 63 is connected to the crushing section 60 by a pipe 62, and draws the crushed material obtained by the crushing section 60 together with the inactivation aqueous solution B from the crushing section 60 (mixed solution 92), and sends the crushed material to the next process. However, the crushed material includes materials including pulp fibers, superabsorbent polymers, materials of the collection bag A, films, nonwoven fabrics, elastic bodies, etc.

The first separation device 13 stirs the mixed solution 92 which includes the crushed material obtained by the crushing device 12 and the inactivation aqueous solution, and while performing the washing so as to remove dirt (waste, etc.) from the crushed material from the mixed solution 92, separates the inactivation aqueous solution 93 which includes pulp fibers and superabsorbent polymers, and sends the same to the first dust removal device 14.

As the first separation device 13, for example, a washing machine including a washing and dehydrating tank and a water tank surrounding the washing and dehydrating tank, may be mentioned. However, the washing and dehydrating tank (a rotating drum) is used as a washing and sieving tank (separating tank). As the washing machine, for example, a horizontal-type washing machine ECO-22B (manufactured by Inamoto Co., Ltd.) may be mentioned.

The first dust removal device 14 removes foreign matter present in the inactivation aqueous solution 93 which includes pulp fibers and superabsorbent polymers by a screen having a plurality of openings, and forms an inactivation aqueous solution 94 which includes pulp fibers and superabsorbent polymers which have little foreign matter. As the first dust removal device 14, for example, a screen separator (a coarse screen separator), and more specifically, for example, a pack pulper (manufactured by Satomi Corporation), may be mentioned.

The second dust removal device 15 removes finer foreign matter from the inactivation aqueous solution 94 which includes pulp fibers and superabsorbent polymers having little foreign matter, which is delivered from the first dust removal device 14 by a screen having a plurality of openings, and forms an inactivation aqueous solution 95 which includes pulp fibers and superabsorbent polymers having even little foreign matter. As the second dust removal device 15, for example, a screen separator, specifically, for example, Ramoscreen (manufactured by Aikawa Iron Works Co., Ltd.), may be mentioned.

The third dust removal device 16 forms, by centrifugation, an inactivation aqueous solution 96 which includes pulp fibers and superabsorbent polymers with even little foreign matter, from the inactivation aqueous solution 95 which includes pulp fibers and superabsorbent polymers with little foreign matter, delivered from the second dust removal device 15. As the third dust removal device 16, for example, a cyclone separator, specifically, an ACT low concentration cleaner (manufactured by Aikawa Iron Works Co., Ltd.), may be mentioned.

The second separation device 17 separates the inactivation aqueous solution 96 which includes pulp fibers and superabsorbent polymers, which has little foreign matter and is sent from the third dust removal device 16, into pulp fibers 97 which include the remaining inactivation aqueous solution and superabsorbent polymers and an inactivation aqueous solution 100 which includes superabsorbent polymers, by a screen having a plurality of openings. As the second separation device 17, for example, a drum screen separator, specifically, for example, a drum screen dehydrator (manufactured by Toyo Screen Co., Ltd.), may be mentioned.

The third separation device 18, While separating the pulp fibers 97 delivered from the second separation device 17 into a solid 98 which includes the pulp fibers and the superabsorbent polymers and a liquid which includes the remaining superabsorbent polymers and the inactivation aqueous solution, by a screen having a plurality of openings, applies pressure to the solid so as to crush the superabsorbent polymers in the solid. As the third separation device 18, for example, a screw press dehydrator, specifically, for example, a screw press dehydrator (manufactured by Kawaguchi Seiki Co., Ltd.), may be mentioned.

The ozone treatment device 19 treats the solid 98 delivered from the third separation device 18 with an ozone aqueous solution which includes ozone. Thereby, the superabsorbent polymers are oxidized and decomposed, the superabsorbent polymers are removed from the pulp fibers, and the ozone aqueous solution 99 which includes the recycled pulp fibers is discharged.

The fourth separation device 20 separates the recycled pulp fibers from the ozone aqueous solution 99 treated by the ozone treatment device 19 by using a screen having a plurality of openings. As the fourth separation device 20, for example, a screen separator may be mentioned.

The fifth separation device 21, the ozone treatment device 22, the pH adjustment device 23, and the water storage tank 24 are devices for regenerating and reusing the inactivation aqueous solution used in the system 1.

The fifth separation device 21 forms the inactivation aqueous solution 101 from which the superabsorbent polymers are removed from the inactivation aqueous solution 100 which includes the superabsorbent polymers by using a screen separator, etc.

The ozone treatment device 22 sterilizes the inactivation aqueous solution 101 from which the superabsorbent polymers have been removed with ozone so as to form the inactivation aqueous solution 102 which has been subjected to the sterilizing treatment. The pH adjusting device 23 adjusts the inactivation aqueous solution 102 which has been subjected to the sterilizing treatment to have a predetermined pH so as to form a regenerated inactivation aqueous solution 103. The water storage tank 24 stores an excess of the inactivation aqueous solution 103 that has been regenerated.

EXAMPLES

The present disclosure is described below by way of examples, however, the disclosure is not limited to these examples.

Production Example 1

According to the flow chart shown in FIG. 3, an inactivation aqueous solution No. 1 in which a total of 10 inactivation steps (inactivation step S201×10 times) were performed was obtained. The organic acid was citric acid, the absorbent article was a used disposable diaper, and the superabsorbent polymers were those of sodium polyacrylate-based. The initial pH of the inactivation aqueous solution (first time) was adjusted to 2.0, and the pH of the inactivation aqueous solution (second to tenth time) was adjusted to approximately 3.0 in the pH adjustment step S204.

Prior to the pH adjustment step S204, the inactivation aqueous solution No. 1 was subjected to the sterilization step S206 so that the number of common bacteria was less than 10 bacteria/mL with ozone, and after the first, fifth and tenth sterilization steps were completed, the samples of the inactivation aqueous solution No. 1 (once, five and ten times) were sampled with the passage of time. Further, in the first to tenth inactivation steps, the inactivated superabsorbent polymers were sampled.

Analysis revealed that the inactivation aqueous solution No. 1 included 2.7% by mass of citric acid.

Production Example 2

Inactivation aqueous solution No. 2 was prepared in the same manner as in Production Example 1 except that the sterilization step S206 was not performed.

Incidentally, in the inactivation aqueous solution No. 2, after the first, fifth and tenth inactivation steps were completed, the samples of the inactivation aqueous solution No. 2 (once, five and ten times) ere sampled with the passage of time.

Analysis revealed that the inactivation aqueous solution No. 2, which had been subjected to a total of 10 inactivation steps, included 2.3% by mass of citric acid.

Examples 1 and 2

The number of general bacteria in each samples of the inactivation aqueous solution No. 1 and inactivation aqueous solution No. 2 over time (once, five and ten times) was measured.

The results are given in FIG. 6.

The absorption magnification (mass ratio) of the inactivated superabsorbent polymers sampled in Production Example 1 was as follows.

First inactivation step S201: approximately 7.0 times
Second to Tenth inactivation steps S201: approximately 22.0 times As shown in FIG. 6, the number of general bacteria was 0 bacteria/g in the inactivation aqueous solution No. 1 in any of the samples over time (the number of general bacteria in the undiluted sample itself was 0 bacteria/g). In addition, the samples (once, five and ten times) over time of the inactivation aqueous solution No. 1 had less coloration and odor than the samples (once, five and ten times) over time of the inactivation aqueous solution No. 2, respectively.

Thus, when the number of concentration elevation steps is increased and recycled pulp fibers are produced, it is suggested that the concentration elevation step preferably includes the sterilization step.

Further, the absorption magnifications of the inactivated superabsorbent polymers in each of the second to tenth inactivation steps S201 of Production Example 1 were approximately 22.0 times. From this, it can be understood that the inactivation property of the superabsorbent polymers is determined by the pH of the inactivation aqueous solution, and it is difficult for the same to be affected by the concentration elevation step S205 (the effect of the discharged excrement).

Production Example 3

Precipitation Step S101

Sodium hydroxide (in a solid state) was added to 2,000 g of inactivation aqueous solution No. 1 so as to adjust the pH to 7. Next, 32 g of calcium chloride as a metal salt was dissolved in the inactivation aqueous solution No. 1 while stirring the inactivation aqueous solution No. 1, (i) calcium citrate as a water-insoluble salt of an organic acid was precipitated, and (ii) a fine solid excrement was coagulated.

Mixture Collection Step S102

After left still for 24 hours after addition of calcium chloride, by solid-liquid separation of the inactivation aqueous solution No. 1 using a mesh filter, a mixture (wet state) of (i) calcium citrate (tetrahydrate) as a water-insoluble salt of an organic acid, and (ii) solid excrement was obtained, and 120 g of the mixture (dry state) was obtained by drying the mixture (wet state) at 120° C. for 10 minutes.

Organic Acid Generation Step S103

30% by mass of sulfuric acid aqueous solution as a free organic acid generating acid was added to a mixture of (i) calcium citrate as a water-insoluble salt of an organic acid and (ii) solid excrement, so as to be 1.0 time equivalent to 120 g of calcium citrate (tetrahydrate). Specifically, assuming that 120 g of the mixture (dry state) is all calcium citrate (tetrahydrate) (=0.21 mol), 30 mass % of sulfuric aqueous solution is added to the above-mentioned the mixture (dry state) so that the total molar number of $H^+$ thereof is 1.26 mol (molar number of sulfuric acid is 0.63 mol) which is 1.0 time equivalent to 1.26 mol being the total molar number of carboxyl groups present in 0.21 mol of calcium citrate (tetrahydrate).

In the mixture aqueous solution, (vi) precipitation of calcium sulfate as a water-insoluble salt was formed by addition of 30% by mass of sulfuric acid aqueous solution.

Organic Acid Solution Obtainment Step S104

By the solid-liquid separation of the mixture aqueous solution using a mesh filter, approximately 65 g of a citric aqueous solution as an organic acid aqueous solution was obtained. The pH of the citric acid aqueous solution was 2.1.

REFERENCE SIGNS LIST

S1 inactivation step
S2 superabsorbent polymer removal step
S3 pH adjustment step
S4 concentration elevation step
S5 sterilization step
S6 organic acid recovery step
S101 precipitation step
S102 mixture collection step
S103 organic acid generation step
S104 organic acid solution obtainment step
S201 inactivation step
S202 material extraction step
S203 recycled pulp fiber formation step
S204 pH adjustment step
S205 concentration elevation step
S206 sterilization step
S207 organic acid recovery step
11 rupturing device
12 crushing device
13 first separation device
14 first dust removal device
15 second dust removal device
16 third dust removal device
17 second separation device
18 third separation device
19 ozone treatment device
20 fourth separation device
21 fifth separation device
22 ozone treatment device
23 pH adjustment device
24 water storage tank

The invention claimed is:

1. A method of recovering an organic acid which inactivates superabsorbent polymers included in a used absorbent article, the method comprising:
   (1) an inactivation step of immersing the used absorbent article or superabsorbent polymers obtained from the used absorbent article in an inactivation aqueous solution which has a predetermined pH and includes an organic acid to form a first solution that includes the inactivation aqueous solution and inactivated superabsorbent polymers;
   (2) a superabsorbent polymer removal step of removing the inactivated superabsorbent polymers from the first solution produced by step (1) to form a second solution that includes the inactivation aqueous solution;
   (3) a pH adjustment step of adjusting the pH of the second solution produced by step (2) to form a regenerated inactivation solution having a predetermined pH;
   a concentration elevation step of repeating at least once steps (1)-(3) by circulating the regenerated inactivation solution produced by step (3) to the inactivation step (1) to produce a concentration elevation solution; and recovering organic acid from the concentration elevation solution.

2. The method according to claim 1, wherein
in the pH adjustment step, the second solution is adjusted to have the predetermined pH by adding an organic acid, removing a pH raising substance which raises pH, or a combination of the adding and the removing.

3. The method according to claim 2, wherein
the organic acid is an organic acid which includes a carboxyl group.

4. The method according to claim 1, wherein
the concentration elevation step further includes a sterilization step of sterilizing the regenerated inactivation aqueous solution.

5. The method according to claim 4, wherein
in the sterilization step, the regenerated inactivation aqueous solution is sterilized by using ozone, chlorine dioxide, hydrogen peroxide, ultraviolet light, radiation, or any thereof.

6. The method according to claim 4, wherein
in the sterilization step, the regenerated inactivation aqueous solution is sterilized by using ozone and deep ultraviolet light.

7. A method of producing recycled pulp fibers from a used absorbent article while elevating a concentration of and recovering an organic acid which inactivates superabsorbent polymers, the method comprising:
   (1) an inactivation step of by immersing a material which includes pulp fibers and superabsorbent polymers derived from the used absorbent article in an inactivation aqueous solution which has a predetermined pH and includes an organic acid to form a first solution that includes the inactivation aqueous solution and inactivated material;
   (2) a material extraction step of extracting the inactivated material from the first solution produced by step (1) to form a second solution that includes the inactivation aqueous solution;
   (3) a recycled pulp fiber formation step of obtaining the recycled pulp fibers from the inactivated material extracted in step (2);
   (4) a pH adjustment step of adjusting the pH of the second solution produced by step (2) to form a regenerated inactivation solution having a predetermined pH;
      a concentration elevation step of repeating at least once steps (1)-(4) by circulating the regenerated inactivation solution produced by step (4) to the inactivation step (1) to produce a concentration elevation solution; and
   recovering organic acid from the concentration elevation solution.

8. The method according to claim 7, wherein
in the pH adjustment step, the second solution is adjusted to have the predetermined pH by adding an organic acid, removing a pH raising substance which raises pH, or a combination of the adding and the removing.

9. The method according to claim 8, wherein the organic acid is an organic acid which includes a carboxyl group.

10. The method according to claim 7, wherein
the concentration elevation step further includes a sterilization step of sterilizing the regenerated inactivation aqueous solution.

11. The method according to claim 10, wherein
in the sterilization step, the regenerated inactivation aqueous solution is sterilized by using ozone, chlorine dioxide, hydrogen peroxide, ultraviolet light, radiation, or any combination thereof.

12. The method according to claim 10, wherein
in the sterilization step, the regenerated inactivation aqueous solution is sterilized by using ozone and deep ultraviolet light.

* * * * *